United States Patent
Bonds

[19]

[11] Patent Number: 5,947,936
[45] Date of Patent: Sep. 7, 1999

[54] SYRINGE WITH SPRING BIASED NEEDLE COVER

[76] Inventor: Michael F. Bonds, 190 Huntview Dr., Brandon, Miss. 39042

[21] Appl. No.: 09/178,258

[22] Filed: Oct. 23, 1998

[51] Int. Cl.$^6$ .................................................. A61M 5/00
[52] U.S. Cl. ........................................... 604/263; 604/198
[58] Field of Search .................................... 604/263, 198, 604/192, 187, 110, 134–136

[56] References Cited

U.S. PATENT DOCUMENTS

| | | | |
|---|---|---|---|
| 2,876,770 | 3/1959 | White | 128/215 |
| 3,134,380 | 5/1964 | Armao | 128/215 |
| 4,601,708 | 7/1986 | Jordan | 604/136 |
| 4,787,891 | 11/1988 | Levin et al. | 604/136 |
| 4,804,371 | 2/1989 | Vaillancourt | 604/198 |
| 4,929,237 | 5/1990 | Medway | 604/198 |
| 5,049,136 | 9/1991 | Johnson | 604/198 |
| 5,360,408 | 11/1994 | Vaillahcourt | 604/198 |
| 5,403,286 | 4/1995 | Lockwood, Jr. | 604/110 |
| 5,527,294 | 6/1996 | Weatherford et al. | 604/198 |
| 5,634,906 | 6/1997 | Haber et al. | 604/198 X |

*Primary Examiner*—John D. Yasko
*Attorney, Agent, or Firm*—Joseph N. Breaux

[57] ABSTRACT

A syringe with a spring biased needle cover that is biased into a fully extended position by the biasing spring to automatically cover the needle of the syringe. The syringe includes a syringe plunger, a syringe body and a cover assembly including a needle tube with a biasing spring positioned therein and a locking tab extending outwardly at an angle therefrom and a slidable needle cover member slidably positioned over the end of the needle tube and lockable in the fully extended position by the locking tab; the locking tab being depressible against the needle tube to allow the cover member to slide over the needle to reveal the needle for use; the biasing spring biasing the cover member back into the fully extended position covering the end of the needle when a retracting force supplied by the user is removed; the needle tube including two guide slots formed through the sidewall thereof; the cover member including two retaining tabs, each of the retaining tabs being slidably entrapped within one of the guide slots.

3 Claims, 4 Drawing Sheets

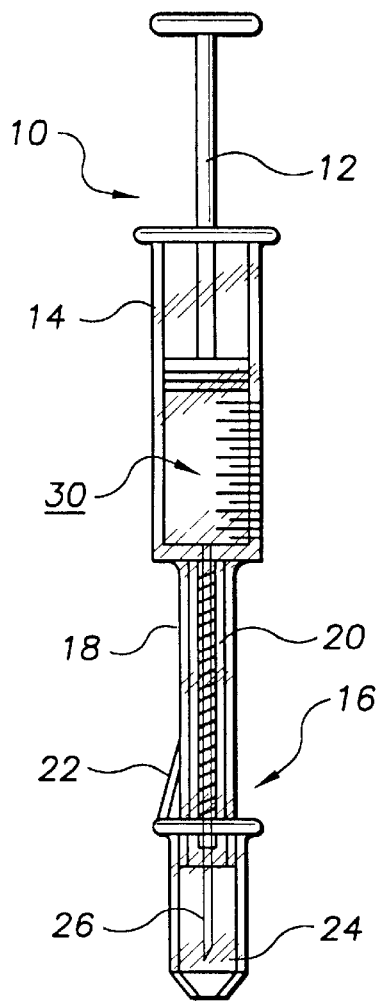
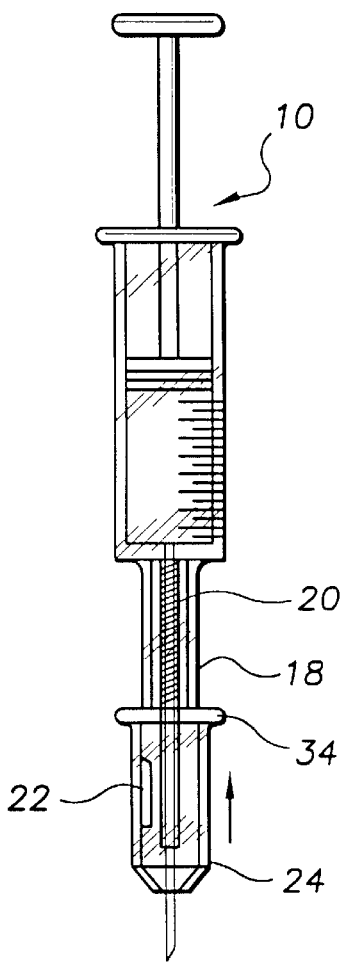
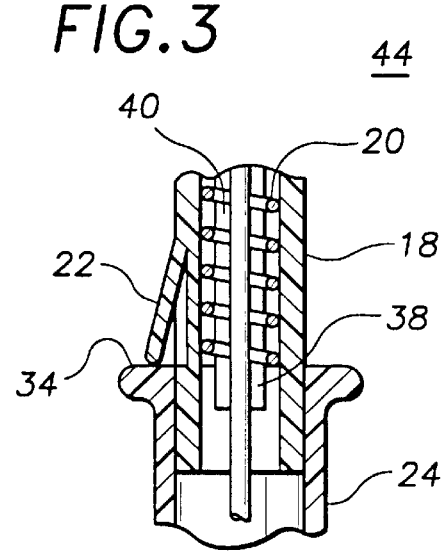

SYRINGE WITH SPRING BIASED NEEDLE COVER

TECHNICAL FIELD

The present invention relates to medical equipment and more particularly to a syringe having a spring biased needle cover that is biased into a fully extended position by the biasing spring to automatically cover the needle of the syringe; the syringe including a syringe plunger, a syringe body and a cover assembly including a needle tube with a biasing spring positioned therein and a locking tab extending outwardly at an angle therefrom and a slidable needle cover member slidably positioned over the end of the needle tube and lockable in the fully extended position by the locking Lab; the locking tab being depressible against the needle tube to allow the cover member to slide over the needle to reveal he needle for use; the biasing spring biasing the cover member back into the fully extended position covering the end of the needle when a retracting force supplied by thee user is removed; the needle lube including two guide slots formed through the sidewall thereof; the cover member including two retaining tabs, each of the retaining tabs being slidably entrapped within one of the guide slots.

BACKGROUND OF INVENTION

Many diseases are transmitted through the contact with the blood of a carrier. This contact can occur when the skin of a health care worker is accidentally punctured or pricked by the needle of a syringe that has been used on a carrier. Although precautions are taken to prevent such contact with the needle, many health care workers are contaminated in this manner. It would be a benefit, therefore, to have a syringe that included a needle cover member that was biased into a needle covering position that did not require the health care worker to deploy the needle cover after use of the syringe. Because children and other people can come into contact with medical waste, it would be a further benefit to have a syringe including a cover member that was automatically deployed and locked in the deployed position after use.

SUMMARY OF INVENTION

It is thus an object of the invention to provide a syringe with spring biased needle cover.

It is a further object of the invention to provide a syringe with spring biased needle cover that Is biased into a needle covering position and that automatically deploys once a retracting force supplied by the health care worker is removed.

It is a still further object of the Invention to provide a syringe with spring biased needle cover that is automatically locked in the deployed position after use.

It is a still further object of the invention to provide a syringe with spring biased needle cover that is biased into a fully extended position by the biasing spring to automatically cover the needle of the syringe; the syringe including a syringe plunger, a syringe body and a cover assembly including a needle tube with a biasing spring positioned therein and a locking tab extending outwardly at an angle therefrom and a slidable needle cover member slidably positioned over the end of the needle tube and lockable in the fully extended position by the locking tab; the locking tab being depressible against the needle tube to allow the cover member to slide over the needle to reveal the needle for use; the biasing spring biasing the cover member back into the fully extended position covering the end of the needle when a retracting force supplied by the user is removed; the needle tube including two guide slots formed through the sidewall thereof; the cover member including two retaining tabs, each of the retaining tabs being slidably entrapped within one of the guide slots.

It is a still further object of the invention to provide a syringe with spring biased needle cover that accomplishes all or some of the above objects in combination.

Accordingly, a syringe with spring biased needle cover is provided. The syringe with spring biased needle cover includes a syringe plunger, a syringe body and a cover assembly including a needle tube with a biasing spring positioned therein and a locking tab expending outwardly al an angle therefrom and a slidable needle cover member slidably positioned over the end of the needle tube and lockable in the fully extended position by the locking tab; the locking tab being depressible against the needle tube to allow the cover member to slide over the needle to reveal the needle for use; the biasing spring biasing the cover member back into the fully extended position covering the end of the needle when a retracting force supplied by the user is removed; the needle tube including two guide slots formed through the sidewall thereof; the cover member including two retaining tabs, each of the retaining tabs being slidably entrapped within one of the guide slots.

BRIEF DESCRIPTION OF DRAWINGS

For a further understanding of the nature and objects of the present invention, reference should be made to the following detailed description, taken in conjunction with the accompanying drawings, in which like elements are given the same or analogous reference numbers and wherein:

FIG. 1 is a side plan view of an exemplary embodiment of the syringe with spring biased needle cover of the present invention showing the syringe plunger, the syringe body and the cover assembly including the needle tube with the spring positioned therein and the locking tab extending outwardly at an angle therefrom and the slidable needle cover member slidably positioned over the end of the needle tube and locked in the fully extended position by the locking tab.

FIG. 2 is a second side plan view of syringe with spring biased needle cover of FIG. 1 showing the locking tab depressed against the needle tube and positioned within the needle cover to allow the needle cover to be moved Into the fully retracted position against the biasing force of the spring to expose the needle of the syringe for use.

FIG. 3 is a cross-sectional detail view of the syringe of FIG. 1 showing the end of the need e tube including one of the two guide slots formed through the sidewall of the needle tube, the hypodermic needle and the spring positioned within the tubular pathway, of the needle tube, and the locking tab extending outwardly from the side of the needle tube and in locking contact with the upper rim of the cover member; and the upper end of the cover member showing one of the two retaining tabs slidably entrapped within the guide slot and the finger ledge formed around the upper rim of the cover member.

EXEMPLARY EMBODIMENTS

Figure 4:
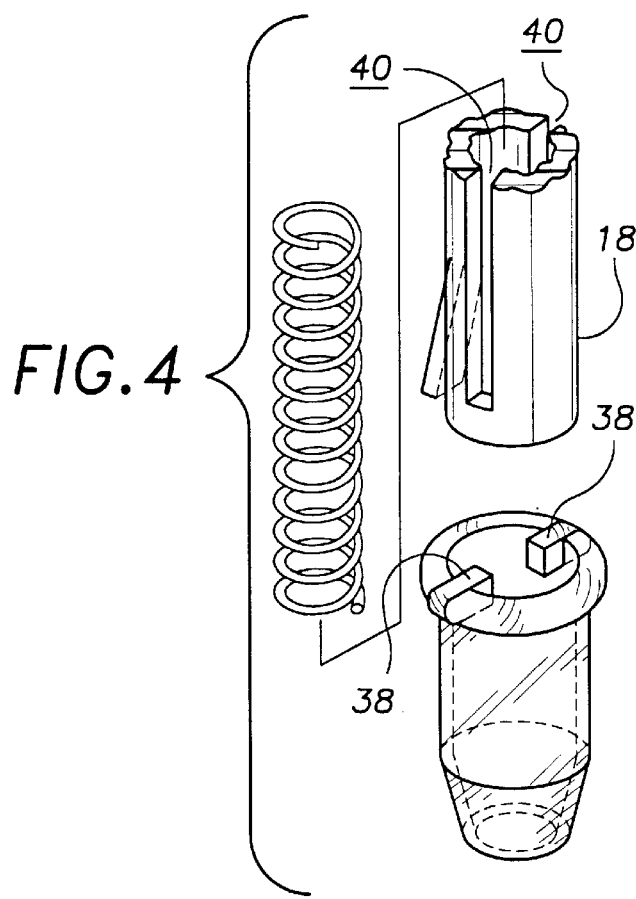
FIG. 4 is an exploded partial perspective view showing the end or the needle tube including the locking tab and the two guide slots formed through the sidewall of the needle tube; the biasing spring removed from the tubular pathway of the needle tube; and the cover member with the tapered tip end terminating in the needle opening, the two retaining tabs adhesively secured to the upper rim of the cover member and extending into the needle tube receiving opening.

FIG. 1 shows an exemplary embodiment of the syringe with spring biased needle cover of the present invention, generally designated by the numeral 10. In this embodiment syringe 10 includes a conventional syringe plunger 12, a conventional syringe body 14 and a cover assembly, generally designated 16. Cover assembly 16 includes a needle tube 18 that is integrally formed with the end of syringe body 14 and that includes a biasing spring 20 positioned therein and a Locking tab 22 extending outwardly at an angle therefrom; and a slidable needle cover member 24 that extends past a hypodermic needle 26 that is positioned through needle tube 18 and in connection with the medicine reservoir 30 formed within syringe body 14.

Figure 5:
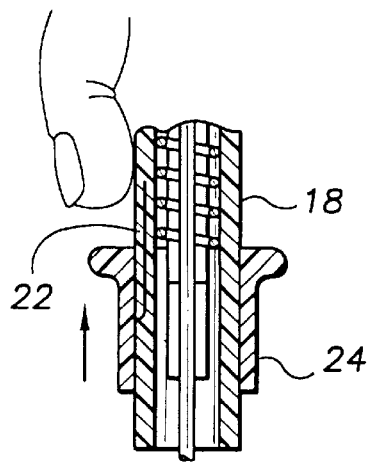
FIG. 5 is a cross-section detail view showing the locking tab depressed against the side of the needle tube and the cover member released to slide upward along the needle tube against the force of the biasing spring.
Figure 6:
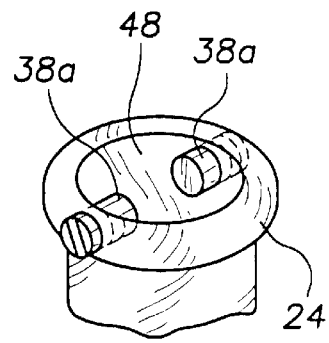
FIG. 6 is a partial perspective view showing a second exemplary embodiment of the retaining tabs threaded through the sidewall of the cover member and into the tube receiving opening.

With reference to FIG. 2, prior to use of syringe 10 locking tab 22 is depressed against needle tube 18 and cover member 24 retracted against the biasing force of biasing spring 20 by grasping the extended rim edge 34 of cover member 24. With reference to FIG. 3, after use biasing spring 20 exerts a force against the retaining Labs 38 (both shown in FIG. 4) and forces cover member 24 downward until retaining tabs 38 contact the end of the two guide slots 40 (more clearly shown in FIG. 4) formed through the sidewall of needle tube 8 Ac the point where retaining tabs 38 contact the end of the two guide slots 40 the tip end of locking tab 22 clears the rim edge 34 of cover member 24 and resiliently extends away from needle tube 18 locking cover member 24 in the fully extended position. FIG. 5 shows locking tab 22 depressed against the sidewall of needle tube 18 and positioned within cover member 24. FIG. 6 snows a second exemplary embodiment of the retaining tabs 38a. In this second embodiment, retaining tabs 38a screw into cover member 24 and into the needle tube receiving opening 48.

Figure 7:
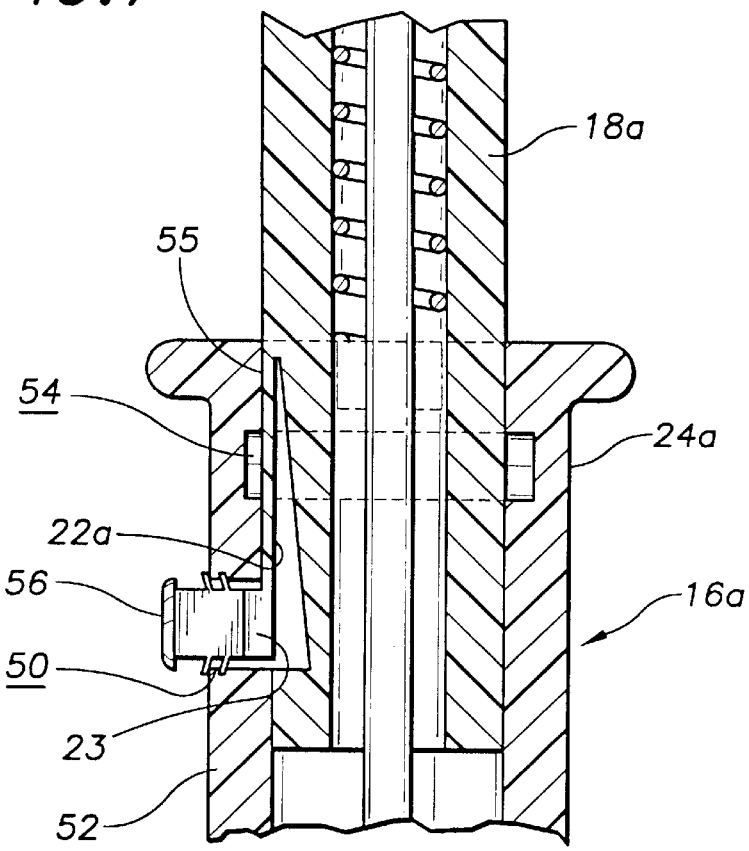
FIG. 7 is a cross-sectional detail view showing a second exemplary locking arrangement for the cover member including a needle tube having a resilient locking tab with a locking nodule formed it the end thereof and a cover member having a first locking nodule hole formed entirely through the sidewall thereof, a second locking nodule hole formed partially into an interior wall thereof, and a disengagement plug inserted into the exterior to the first locking nodule hole to the first predetermined depth to allow the locking nodule to be received into first locking nodule hole.
Figure 8:
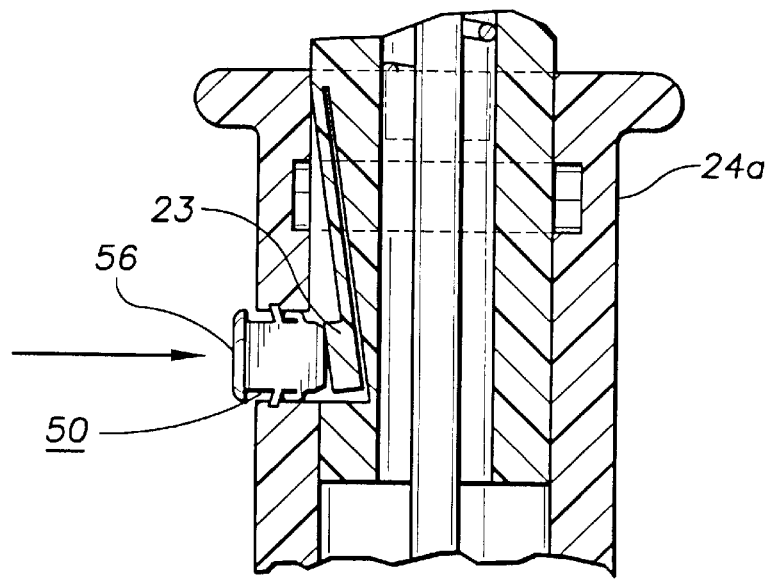
FIG. 8 is a cross-sectional detail view showing the second exemplary locking arrangement for the cover member of figure 7 with the disengagement plug inserted into the exterior of the first locking nodule hole to the second predetermined depth to entirely prevent the locking nodule from being inserted into the first locking nodule hole and the cover member positioned in the fully extended position.
Figure 9:
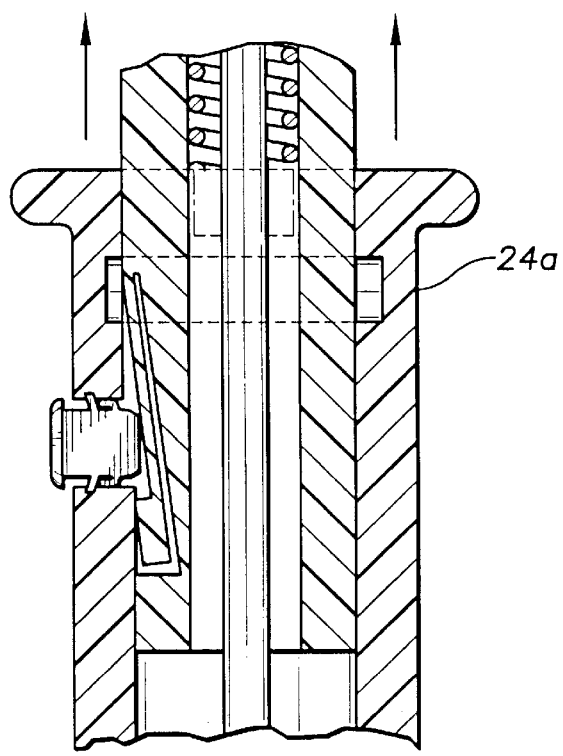
FIG. 9 is a cross-sectional detail view showing the second exemplary locking arrangement for the cover member of FIG. 7 with the disengagement plug inserted into the exterior of the first locking nodule hole to the second predetermined depth to entirely prevent the locking nodule from being inserted into the first locking nodule nose and the cover member in the fully retracted position.
Figure 10:
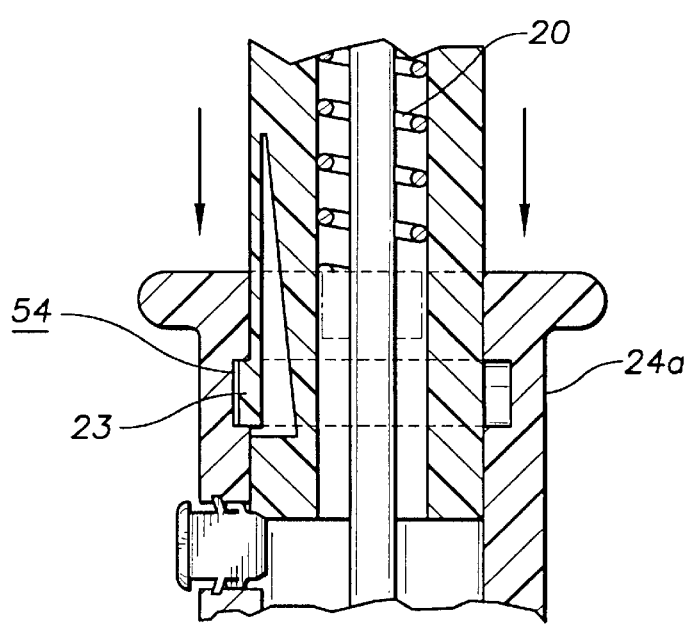
FIG. 10 is a cross-sectional detail view showing the second exemplary locking arrangement for the cover member of FIG. 7 with the disengagement plug inserted into the exterior of the first locking nodule hole to the second predetermined depth to entirely prevent the locking nodule from being inserted into the first locking nodule hole and the cover member moved into the discarding position with the locking nodule permanently locked within the second locking nodule hole.
Figure 11:
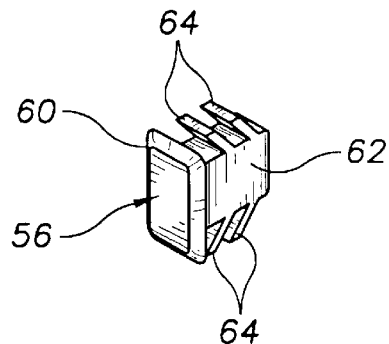
FIG. 11 is a detail perspective view of the disengagement plug showing the head portion and the insertion shaft with the two sets of gripping flaps extending outwardly therefrom.

With reference now to FIG. 7, in a second exemplary embodiment the cover assembly 16a is provided with a permanent locking arrangement that is activated when cover member 24a is retracted for use. In this embodiment, the locking arrangement for cover member 24a includes a needle tube 18a having a resilient locking tab 22a with a locking nodule 23 formed at the end thereof and a cover member 24a having a first locking nodule hole 50 formed entirely through the sidewall 52 thereof, a second locking nodule hole 54 formed partially into an interior wall 55 thereof, and a disengagemet plug 56. During assembly, disengagement plug 56 is inserted into the exterior of first locking nodule hole 50 to a first predetermined depth, al. is sufficient to allow locking nodule 23 to be received into first locking nodule hole 50. With reference now to FIG. 8, cover member 24a is released by depressing disengagement plug 56 fully into first locking nodule hole 50 until a second predetermined depth is reached. At the second predetermined depth, disengagement plug 56 completely fills first locking nodule hone 50 and prevents locking nodule 23 from being inserted therein. At this point cover member 24a is free to be retracted as shown in FIG. 9. Referring to FIG. 10, when cover member 24a is released, biasing forces from biasing spring 20 force cover member 24a downward until Locking nodule 23 engages second locking nodule hole 54. FIG. 11 shows disengagement plug 56 in isolating including the head portion 60 and the insertion shaft 62 with the two sets of gripping flaps 64 that extend outwardly therefrom.

It can be seen from the preceding description that a syringe with a spring biased needle cover has been provided that includes a cover member that is biased into a needle covering position and hat automatically deploys once a retracting force supplied by the health care worker is removed; that includes a cover member that is automatically locked in the deployed position after use; and that includes a syringe plunger, a syringe body and a cover assembly including a needle tube with a biasing spring positioned therein and a locking tab extending outwardly at an angle therefrom and a slidable needle cover member slidably positioned over the end of the needle tube and lockable in The fully extended position by the Locking tab; the locking tab being depressible against the needle tube to allow the cover member to slide over the needle to reveal the needle for use; the biasing spring biasing the cover member back into the fully extended position covering the end of the needle when a retract rig force supplied by the user is removed; the needle tube including two guide slots formed through the sidewall thereof; the cover member including two retaining tabs, each of the retaining tabs being slidably entrapped within one of the guide slots.

It is noted that the embodiment of the syringe with spring biased needle cover described herein in detail for exemplary purposes is of course subject to nary different variations in structure, design, application and methodology. Because many varying and different embodiments may he made within the scope of the inventive concept(s) herein taught, and because many modifications may be made in The embodiment herein detailed in accordance with the descriptive requirements of the law, it is to be understood that the details herein are to be interpreted as illustrative and not in a limiting sense.

What is claimed is:

1. A syringe with spring biased needle cover comprising:

a syringe body;

a syringe plunger slidable within said syringe body; and a cover assembly slidable over said syringe body and including a needle tube and a slidable cover member;

said needle tube having a biasing spring positioned wherein and a locking tab extending outwardly at an angle therefrom;

said slidable needle cover member being slidably positioned over an end of the needle tube and lockable in a fully extended position by said locking tab;

said locking tab being depressible against said needle tube to allow said cover member no slide over a needle to reveal the needle for use;

said biasing spring biasing said cover member back into said fully extended position covering tho end of the needle when a retracting force supplied by the user is removed;

said needle tube including two guide slots formed through a sidewall thereof;

said cover member including two retaining tabs, each of said retaining tabs being slidably entrapped within one of said guide slots.

2. The syringe with spring biased needle cover of claim 1, further comprising:

a permanent locking arrangement that is activated when said cover member is retracted for use;

said permanent locking arrangement includes a resilient locking tab formed in connection with said needle tube and having a locking nodule formed at the end thereof; a first locking nodule hole formed entirely through a sidewall of said a cover member; a second locking nodule hole formed partially into an interior wall of said a cover member; and a disengagement plug;

said disengagement plug being inserted into an exterior opening of said first socking nodule hole to a first predetermined depth that is sufficient to allow said locking nodule to be received into said first locking nodule hole;

said cover member being released by depressing said disengagement plug fully into said first locking nodule hole until a second predetermined depth is reached, at said second predetermined depth, said disengagement plug completely filling said first locking nodule hole and preventing said locking nodule from being inserted therein.

3. The syringe with spring biased needle cover of claim 2, wherein:

said disengagement plug includes a head portion and an insertion shaft provided with two sets of gripping flaps that extend outwardly therefrom.

\* \* \* \* \*